United States Patent [19]
Rudoff et al.

[11] 3,950,441
[45] Apr. 13, 1976

[54] PROCESS AND CATALYST FOR PREPARING 1,4-BUTANEDIOL

[75] Inventors: Stanley Rudoff, Elizabeth; Waldo DeThomas, Parsippany, both of N.J.

[73] Assignee: GAF Corporation, New York, N.Y.

[22] Filed: Mar. 30, 1973

[21] Appl. No.: 346,657

Related U.S. Application Data

[62] Division of Ser. No. 72,870, Sept. 16, 1970, Pat. No. 3,759,845.

[52] U.S. Cl............................................. 260/635 M
[51] Int. Cl.² ........................................ C07C 29/00
[58] Field of Search ............................. 260/635 M

[56] References Cited
UNITED STATES PATENTS 3,449,445   6/1969   Wetherill.................... 260/635 M
3,479,411   11/1969  Adam et al.................. 260/635 M
3,759,845   9/1973   Rudoff........................ 260/635 M

FOREIGN PATENTS OR APPLICATIONS 1,529,356   5/1968   France ....................... 260/635 M Primary Examiner—Joseph E. Evans
Attorney, Agent, or Firm—Walter C. Kehm

[57] ABSTRACT

An improved hydrogenation catalyst is provided comprising a high surface area amorphous or gamma alumina support carrying thereon from about 12 to about 20% by weight of nickel, about 1 to about 10% by weight of copper and from 0 to about 1.5% by weight of manganese. This catalyst is used as a second stage catalyst in the two stage hydrogenation of 1,4-butynediol to 1,4-butanediol.

3 Claims, No Drawings

PROCESS AND CATALYST FOR PREPARING 1,4-BUTANEDIOL

This is a division of application Serial No. 72,870 filed Sept. 16, 1970 now U.S. Pat. No. 3,759,845.

This invention relates to an improved process for the preparation of 1,4-butanediol from 1,4-butynediol and to an improved hydrogenation catalyst and process therefor.

The hydrogenation of 1,4-butynediol to 1,4-butanediol in the presence of a number of different catalysts and by different procedures is well known in the art.

For example, 1,4-butynediol can be directly converted to 1,4-butanediol in a continuous high pressure process. This process generally comprises feeding 1,4-butynediol to a reactor containing a fixed bed catalyst comprising, nickel, copper and manganese, on a granular silica carrier. Concurrently, hydrogen gas is added to the reactor converting the 1,4-butynediol to 1,4-butanediol as the concurrent streams contact the catalyst. The reaction is conducted at temperatures ranging from about 40° to 140°C and at hydrogen pressures of from about 2,000 to 3,000 psig. The mixed gas and liquid effluent from the reactor are separated, the gas is recycled to the reactor together with make-up hydrogen, and the liquid portion is partly recycled as dilution to the fresh feed and partly fed to a distillation zone for recovery of the 1,4-butanediol.

In this high pressure process, however, the operating conditions as well as the product quality vary with the age of the catalyst employed.

An improved process for the conversion of 1,4-butynediol to 1,4-butanediol is described in U.S. Patent 3,499,445 to Wetherill. The process described therein comprises a partial hydrogenation of a pretreated aqueous solution of 1,4-butynediol of about 35% to 40% concentration from which formaldehyde has been removed by the procedure described in U.S. Pat. No. 2,993,708, at a pH of 6.5 to about 7.5. The solution is fed to a low pressure reactor containing a Raney-type nickel catalyst of the type described in U.S. Pat. No. 1,638,190, which is readily prepared by treating an aluminum alloy with caustic soda to dissolve out the aluminum and leave the nickel in a highly divided form. The amount of catalyst employed is not considered critical since it is not deactivated during the hydrogenation and can be reused many times before being discarded. In general, however, the amount of nickel catalyst employed can vary from about 1 to about 4% by weight of the 1,4-butynediol solution charged. After the 1,4-butynediol solution is charged, the reactor is maintained at a temperature of from about 50° to about 60°C and under a hydrogen pressure of 200 and 300 psig. Contact of the 1,4-butynediol and catalyst is facilitated by agitation. Hydrogenation is continued until the desired partial hydrogenation of the 1,4-butynediol is achieved as determined by the cessation of hydrogen absorption.

The reaction mixture is allowed to settle and the partially hydrogenated product is separated from the catalyst and charged to an intermediate storage zone for pumping into the subsequent high pressure portion of the process. From the intermediate storage zone, the partially hydrogenated solution is charged to a high pressure reactor maintained at about 2,000 to about 3,000 psig at a temperature of about 120° to 140°C. A stream of hydrogen is simultaneously charged under pressure to the reactor. The reactor is filled with a fixed bed of catalyst comprising about 12 to 17% by weight of nickel, 4 to 8% by weight of copper and 0.3 to 1.0% by weight of manganese supported on a silica gel carrier.

The completely hydrogenated liquid product is separated from the residual hydrogen which is recycled together with make-up hydrogen and returned to the reactor. The separated liquid product is then cooled to about room temperature and charged to a storage tank. The product so obtained can then be subjected to distillation and the recovered product, 1,4-butanediol, is obtained in average yields of over 90%.

It has been found, however, that the silica gel carriers heretofore employed as the catalyst supports in the high pressure reactors of the above-described processes physically degrade under the process conditions resulting in the production of fines which cause pressure fluctuations in the high pressure reactor. These pressure fluctuations result in intermittent shut-downs, high catalyst replacement costs and consequent loss of production.

Accordingly, it is an object of the present invention to provide an improved catalyst system for the hydrogenation of 1,4-butynediol to 1,4-butanediol exhibiting longer life and higher activity resulting in longer productivity and improved process economics.

It is another object of the present invention to provide an improved method for preparing a catalyst system of high activity.

It is still another object of the present invention to provide an improved hydrogenation process for the conversion of 1,4-butynediol to 1,4-butanediol in high yields and efficiencies.

These as well as other objects are accomplished by the present invention which provides an improved hydrogenation catalyst for the conversion of 1,4-butynediol to 1,4-butanediol comprising a high surface area, amorphous or gamma alumina carrying thereon from about 12 to about 20% by weight of nickel, from about 1 to about 10% by weight of copper and 0 to about 1.5% by weight of manganese. The alumina supported catalysts of the present invention exhibit high activity and physical stability providing a long catalyst life under process conditions.

In another embodiment of the present invention, there is provided an improved process for the catalytic hydrogenation of 1,4-butynediol to 1,4-butanediol comprising hydrogenating 1,4-butynediol with hydrogen at a temperature of from about 40° to about 175°C and a pressure of from about 1,000 to about 3,000 psig in the presence of a high surface area amorphous or gamma alumina support carrying thereon from about 12 to about 20% by weight nickel, about 1 to about 10% by weight of copper and from 0 to about 1.5% by weight of manganese.

In a further embodiment of the present invention, there is provided an improved process for the catalytic hydrogenation of 1,4-butynediol to 1,4-butanediol comprising partially hydrogenating an aqueous solution of 1,4-butynediol of from about 35 to 40% concentration at a pH of from about 6.0 to about 8.0 with hydrogen at a temperature of from about 50° to 60°C and at a pressure of from about 200 to 300 psig in the presence of a Raney-type nickel catalyst, removing said catalyst and treating the resulting partially hydrogenated 1,4-butynediol (1,4-butenediol) solution with hydrogen at a temperature of from about 120° to 175°C and a pressure of from about 1,000 to about 3,000 psig in the presence of a high surface area amorphous or gamma aluminum support carrying thereon from about 12 to about 20% by weight of nickel, about 1 to about 10% by weight of copper and from 0 to about 1.5% by weight of manganese, and thereafter recovering the 1,4-butanediol.

The catalyst supports of the present invention can be amorphous or gamma aluminas ($Al_2O_3$) capable of exhibiting good physical stability under the hydrogenation process conditions.

As used herein, the term "alumina" is intended to include low silica-containing aluminas, i.e., aluminas containing from 0 to about 10% silica ($SiO_2$). It has been found herein that silica when present in the above amounts is essentially inert and does not affect the performance and physical stability of the catalyst. The properties of silica supports described hereinabove are not manifested in the low silica-containing alumina catalyst supports of the present invention. It has been found that suitable alumina supports exhibit a surface area ranging from about 125 to about 425 square meters per gram, a pore volume of from about 0.25 to about 0.95 cubic centimeters per gram, and a bulk density of from about 0.5 to about 1.25 grams per cc. The catalyst supports can be provided in a wide variety of forms, such as pellets, granules, spheres, extrudates and the like. It is not considered critical to the present invention that the density and pore volume of the support bear a specific relationship to each other; for example, suitable catalysts can be obtained using alumina supports of low density with high pore volume, high density with low pore volume, or any intermediate density with intermediate pore volume. It has been found, in general, that within the limits set forth herein, the catalysts so obtained exhibit high activity and prolonged physical stability under the process conditions.

Any metal salt of manganese, copper and nickel, either organic or inorganic, can be employed for impregnation of the catalyst support, as long as the salt is capable of thermally decomposing to an oxide of the metal, which can then be reduced with hydrogen to the free metal forming the active hydrogenation catalyst. For example, the nitrates, acetates, formates,, and the like, of manganese, copper and nickel have been found useful in the present invention. Most conveniently, a concentrated solution of the combined salts is used for purposes of impregnation of the catalyst support. For example, a concentrated aqueous solution saturated under ambient conditions with respect to the respective salts, was found to contain 61% $Ni(NO_3)_2$, 14% $Cu(NO_3)_2$ and 3% $Mn(NO_3)_2$. Impregnation can be readily accomplished by simply admixing the alumina supports which preferably have been previously degassed, such as by heating at elevated temperatures under vacuum and then cooled to room temperature, with the concentrated salt solution at an elevated temperature such as, for example, from about 75°C to about 115°C, either with or without agitation, for a sufficient period of time to allow the catalyst support to become saturated with the salt solution. Most conveniently, the catalyst can be impregnated by simply heating or dipping the alumina supports in a concentrated solution of the metal salts for a sufficient period of time to allow the catalyst supports to become saturated with the salt solution. After impregnation, the impregnated catalyst can be separated from the residual salt solution by any convenient means, such as by simply filtering, and then washed and dried, such as in a forced air oven, preferably for a sufficient period of time to completely drive off all the water. Preferably, the catalyst is dried in a forced air oven at about 170°C for about 4 hours.

The metal salts of nickel, copper and manganese, impregnated into the catalyst support, are converted to their respective oxides by thermal decomposition effected by calcining the catalyst support in a stream of air at temperatures ranging from about 250°C to about 500°C. The calcining temperature is critical to catalyst activity and should not exceed about 500°C and preferably should range from about 375° to about 425°C. Completeness of calcination can be measured by decomposition of the metal salts to the oxides.

Because of the limited absorption of the respective metal salts by the alumina catalyst support, it may be necessary, in order to obtain the desired metals content of the ultimate catalyst, to repeat the impregnation and calcining procedures several times. By converting the absorbed salts to their respective oxides, the catalyst support is capable of absorbing additional metal salts, thereby raising the ultimate metals content to the desired level. The specific number of times the impregnation-calcination process is repeated is not considered critical and depends primarily upon the ability of the support to absorb the respective metal salts. For example, when a high density, low pore volume support is employed, several absorption-calcination treatments may be necessary to obtain the desired ultimate metals content; whereas, when a low density, high pore volume support is employed, one or two treatments are generally sufficient.

After final calcination, the catalyst exhibits a surface area ranging from about 110 to about 175 square meters per gram, a bulk density ranging from about 0.5 to about 1.25 gms per cc, a pore volume ranging from about 0.25 to about 0.9 cc per gram, and a crushing strength of from about 15 to about 50 pounds.

The catalyst is generated into an active hydrogenation catalyst by reducing the metal oxides contained in the calcined alumina support to the respective free metals with hydrogen. The temperatures for the reduction of the oxides by hydrogenation to the active metal can range from about 250° to about 500°C under hydrogen pressure ranging from about atmospheric to about 1,500 psig. It is considered preferable to reduce the catalyst in thermal gradations, commencing at about 250°C for a period of time sufficient to at least reduce the copper oxides to copper. If copper oxide reduction is conducted at too high temperature, an exotherm occurs which can sinter the copper, thereby adversely affecting the catalyst activity. After the initial heat treatment at 250°, the catalyst can then be heated to from about 300°C to about 500°C for a period of time sufficient to reduce the remaining oxides to their respective free metals. In this manner, catalysts exhibiting optimum activity can be obtained.

Upon reduction of the metal oxides to their respective metals, the quantity of impregnated metals on the alumina support ranges from about 12 to about 20% nickel, about 1 to about 10% copper, and from 0 to about 1.5% manganese. If desired, larger or smaller amounts of the respective metals can be impregnated on the carrier. It has been found, however, that the presence of additional amounts of the metals provides substantially no increase in activity thereby unnecessarily increasing catalyst cost. Conversely, use of smaller amounts of the metals can result in reduced catalyst efficiencies.

The catalysts of the present invention prepared in the manner described above, can be employed to hydrogenate 1,4-butynediol directly or to complete the hydrogenation of partially hydrogenated 1,4-butynediol in the manner described in U.S. Pat. No. 3,449,445. The hydrogenation processes employing the catalysts of the present invention can be conducted at temperatures ranging from about 40°C to about 175°C and preferably from about 120° to about 175°C and at hydrogen pressures ranging from about 1,000 to about 3,000 psig. Through use of the catalysts of the present invention carbonyl numbers of the resulting products are generally below about 1.0.

The following examples further define, describe and compare methods or preparing the improved catalysts of the present invention and the utilizing them in the hydrogenation of 1,4-butynediol to 1,4-butanediol. Parts and percentages are by weight unless otherwise indicated.

EXAMPLE 1

Into a 2-liter round bottom flask fitted with a reflux condenser with a vacuum connection at the top, and a siphon hose was charged 400 grams of pelleted aluminum oxide (alumina). The alumina was degassed by heating at 100°C for 15 minutes at 0.1 mm Hg, then cooled to room temperature. 1,073 g of a nickel nitrate, copper nitrate and manganese nitrate concentrated salt solution containing 61% Ni($NO_3$)$_2$ 14% Cu($NO_3$)$_2$, and 3% Mn($NO_3$)$_2$ was siphoned into the alumina and the mixture heated at 100°C for 1 hour without agitation. After cooling to room temperature, the catalyst mixture was filtered through a Buchner funnel, washed twice with 200 cc of water each time, dried at 110°C for 1 hour, then at 170°C for 4 hours. Under a stream of air, the catalyst was calcined at 375°C to 425°C for 12 hours. The entire procedure was repeated twice more to give a catalyst having a final metals content of 15.0% nickel, 7.8% copper, and 0.5% manganese.

The resulting catalyst was reduced at atmospheric pressure with hydrogen, at three temperature stages, commencing at 250°C and then proceeding to 325°C and ultimately to 400°C for a total of 20 hours. After reduction, a series of hydrogenation experiments were conducted in an autoclave employing 40.7 g of the above catalyst and 400 g of a 35% solution of 1,4-butynediol having a carbonyl number of 48.0. The partially hydrogenated 1,4-butynediol was obtained by first partially hydrogenating 1,4-butynediol with hydrogen in the presence of a Raney-type nickel catalyst until the adsorption of hydrogen ceased. The partially hydrogenated 1,4-butynediol was then fed to the autoclave containing the catalyst obtained as described above. Simultaneously, hydrogen was fed to the autoclave under a pressure of 2,500 psig. After a series of hydrogenations at 150°C the carbonyl numbers from all experiments were less than 1.0 and the physical appearance of the catalyst was excellent, with no fines to be found.

Control

For comparison, a series of runs using the silica gel base catalyst described in U.S. Pat. 3,449,445 were conducted under the identical conditions described hereinabove. The carbonyl numbers from these experiments ranged from 1.0 to 2. After a series of hydrogenations, the recovered catalyst contained fines, the granules had lost their original shape and were easily crushed by mere finger pressure. By comparing the characteristics of the respective hydrogenation processes, it was found that the initial hydrogenation rates were faster and the final carbonyl numbers were lower for the alumina based catalyst of the present invention as compared to the silica gel based catalyst described in said patent.

EXAMPLE 2

Into a 500 cc round bottom flask was charged 87.4 grams of high surface area, low soda aluminum oxide spheres exhibiting the following characteristics:

| | |
|---|---|
| surface area | 380 m$^2$/gm |
| pore volume | 0.51 cm$^3$/gm |
| bulk density | 0.76–0.78 gm/cm$^3$ |
| soda | 0.02% Na$_2$O |
| silica | 0.02% SiO$_2$ |

The flask was connected to a rotating evaporator and the alumina was degassed at 0.1 mm Hg vacuum. 166 g of a concentrated salt solution containing 61% Ni($NO_3$)$_2$, 14% Cu($NO_3$)$_2$, 3% Mn($NO_3$)$_2$ was siphoned into the flask containing the aluminum oxide balls and the mixture heated at 100°C for one hour with slow rotation. After cooling to room temperature, the catalyst was filtered through a Buchner funnel, washed twice with 100 cc of water, dried at 110° for 1 hour, and then at 170°C for 4 hours. Under a stream of air, the catalyst was calcined at 460°C for 16 hours. The entire procedure was repeated two more times to give a catalyst having a total metals content of 15.1% nickel, 5.27% copper and 0.46% manganese. The catalyst was placed in an autoclave and was reduced at 300°C with hydrogen at 1,000 psig. Thereafter, partially hydrogenated 1,4-butynediol was charged to the autoclave together with hydrogen under a pressure of 2,500 psig. The butynediol solution had an initial carbonyl number of 34. On completion of hydrogenation, the 1,4-butanediol obtained exhibited a carbonyl number of less than 1.0 and the physical appearance of the catalyst was excellent.

EXAMPLE 3

Into a 2-liter round bottom flask fitted with a reflux condenser, was charged 400 g of pelleted aluminum oxide and 1,073 g of a concentrated salt solution containing 61% Ni($NO_3$)$_2$, 14% Cu($NO_3$)$_2$, and 3% Mn($NO_3$)$_2$. The mixture was heated at a reflux temperature of about 120°C for 1 hour without agitation. After cooling to room temperature, the catalyst was filtered through a Buchner funnel, washed twice with 200 cc of water, dried at 110°C for 1 hour, and then at 170°C for 4 hours. Under a stream of air, the catalyst was calcined at 375°C for 12 hours. The entire procedure was repeated two more times to give a catalyst having a total metals content of 16.7% nickel, 4.72% copper and 0.44% manganese.

The resulting catalyst was reduced under 2,500 psig hydrogen at a temperature of 250°C and subsequently at 325°C and, finally, at 400°C, for a total period of 20 hours. Thereafter, a series of hydrogenation experiments were conducted employing 47.0 grams of the above catalyst with 400 grams of partially hydrogenated 1,4-butynediol having carbonyl number of 49. The carbonyl numbers after a series of hydrogenation were less than 1.0 and the physical appearance of the catalyst was excellent.

EXAMPLE 4

A catalyst was prepared in the identical manner described in Example 1 resulting in an alumina catalyst support impregnated with 15.0% nickel, 7.8% copper and 0.5% manganese.

The resulting catalyst was reduced at atmospheric pressure with hydrogen, at three temperature stages, commencing at 250°C and then proceeding to 325°C and ultimately to 400°C for a total of 20 hours. After reduction, a series of hydrogenation experiments were conducted in an autoclave employing 48.9 grams of the above catalyst and 400 grams of an aqueous 35% 1,4-butynediol solution exhibiting a carbonyl number of 9.3. Hydrogen was charged to the autoclave and the solution was hydrogenated at 2,500 psig and 150°C until the absorption of hydrogen ceased. Analysis of the hydrogenated product by vapor phase chronotography indicated 100% conversion of the 1,4-butynediol to 1,4-butanediol. After a series of hydrogenation, the physical appearance of the catalyst was excellent and no fines were evident.

EXAMPLES 5 – 7

Employing the identical catalyst and procedure described in Example 4 but varying the hydrogenation temperature and pressure, the effect on the conversion of 1,4-butynediol to 1,4-butanediol was determined. Table I below summarizes the results obtained. It can be seen that the hydrogenation rate is more dependent on temperature than on pressure.

TABLE I

| Example | Temperature (°C) | Hydrogen Pressure (psig) | Conversion of 1,4-butynediol to 1,4-butanediol (%) |
|---------|------------------|--------------------------|-----------------------------------------------------|
| 5 | 150 | 1000 | 100 |
| 6 | 150 | 2500 | 100 |

TABLE I-continued

| Example | Temperature (°C) | Hydrogen Pressure (psig) | Conversion of 1,4-butynediol to 1,4-butanediol (%) |
|---------|------------------|--------------------------|-----------------------------------------------------|
| 7 | 100 | 1000 | 70 |

What is claimed is:
1. In a process for the catalytic hydrogenation of 1,4-butynediol to 1,4-butanediol the improvement which comprises: hydrogenating an aqueous solution of 1,4-butynediol with hydrogen in a twostage process wherein the first stage is conducted in the presence of a hydrogenation catalyst under conditions of temperature and pressure lower than that employed in the second stage to partially hydrogenate said 1,4-butynediol and subjecting said partially hydrogenated 1,4-butynediol to said second stage hydrogenation at a temperature of from about 120° to 175°C and a pressure of from about 1,000 to about 3,000 psig in the presence of a catalyst consisting of a high surface area alumina support carrying thereon approximately by weight 12 to 20% nickel, 1 to 10% copper and 0 to 1.5% manganese.

2. The process of Claim 1 wherein the first stage comprises partially hydrogenating an aqueous solution of 1,4-butynediol of about 35–40% concentration at a pH of from about 6.0 to about 8.0 with hydrogen in the presence of a Raney-type nickel catalyst, at a temperature and pressure substantially lower than the temperature and pressure employed in said second stage; separating said catalyst and the resulting partially hydrogenated 1,4-butynediol solution; treating the separated partially hydrogenated 1,4-butynediol solution with hydrogen at a temperature of from about 120°C to 175°C and a pressure of about 1,000 to 3,000 psig in the presence of a catalyst consisting of a high surface area alummina support carrying thereon approximately by weight 12 to 20% nickel, 1 to 10% copper and 0 to 1.5% manganese and thereafter recovering the 1,4-butanediol.

3. A process as defined in claim 2 wherein hydrogen gas is fed to the reaction system under a pressure of 2,500 psig at a temperature of 150°C.

* * * * *